(12) United States Patent
Nakanishi

(10) Patent No.: US 8,093,284 B2
(45) Date of Patent: Jan. 10, 2012

(54) PROCESS FOR PRODUCING AQUEOUS SOLUTION OF DORIPENEM

(75) Inventor: Hayao Nakanishi, Isaw-gun (JP)

(73) Assignee: Shionogi & Co., Ltd., Osaka (JP)

( * ) Notice: Subject to any disclaimer, the term of this patent is extended or adjusted under 35 U.S.C. 154(b) by 172 days.

(21) Appl. No.: 11/920,998

(22) PCT Filed: May 25, 2006

(86) PCT No.: PCT/JP2006/310437
§ 371 (c)(1),
(2), (4) Date: Nov. 26, 2007

(87) PCT Pub. No.: WO2006/126630
PCT Pub. Date: Nov. 30, 2006

(65) Prior Publication Data
US 2009/0264493 A1    Oct. 22, 2009

(30) Foreign Application Priority Data
May 26, 2005  (JP) ................... 2005-153704

(51) Int. Cl.
*A01N 43/38* (2006.01)
*C07D 411/00* (2006.01)
(52) U.S. Cl. ...................... 514/413; 548/467

(58) Field of Classification Search .............. 514/183
See application file for complete search history.

(56) References Cited

U.S. PATENT DOCUMENTS

| 5,317,016 A | 5/1994 | Nishitani et al. |
| 6,111,098 A * | 8/2000 | Inoue et al. ............... 540/350 |
| 2003/0153191 A1 | 8/2003 | Saitoh et al. |

FOREIGN PATENT DOCUMENTS

| JP | 2004-513749 | 5/2004 |
| WO | 01/72750 | 10/2001 |

OTHER PUBLICATIONS

Nishino et al. (Practical Large-Scale Synthesis of Doripenem: A Novel 1 Beta-Methylcarbapenem Antibiotic, Org. Proc. Res.Dev., 2003,7 (6), pp. 846-850, printed pp. 1-10).*

* cited by examiner

*Primary Examiner* — Sreeni Padmanabhan
*Assistant Examiner* — Timothy E Betton
(74) *Attorney, Agent, or Firm* — Wenderoth, Lind & Ponack, L.L.P.

(57) ABSTRACT

A process for producing an aqueous solution of doripenem while decomposition of doripenem by heat is suppressed is found out.
It was found out that decomposition of doripenem by heat can be suppressed by continuous heating an aqueous suspension of doripenem, and it was found out that an aqueous solution of doripenem can be produced.

7 Claims, 5 Drawing Sheets

PROCESS FOR PRODUCING AQUEOUS SOLUTION OF DORIPENEM

This application is a U.S. National Stage of International Application No. PCT/JP2006/310437, filed May 25, 2006.

TECHNICAL FIELD

The present invention relates to a process for producing an aqueous solution of doripenem. More particularly, the present invention relates to a process for producing an aqueous solution of doripenem comprising continuous heating to dissolve an aqueous suspension of doripenem.

BACKGROUND TECHNIQUE

As an antibacterial agent, a compound having the following structure (hereinafter, referred to as doripenem, (+)-(4R,5S,6S)-6-[(1R)-1-hydroxyethyl]-4-methyl-7-oxo-3-[[(3S,5S)-5-sulfamoylaminomethyl)pyrrolidin-3-yl]thio]-1-az abicyclo[3.2.0]hept-2-ene-2-carboxylic acid) is known (Patent Literature 1).

[Chemical formula 1]

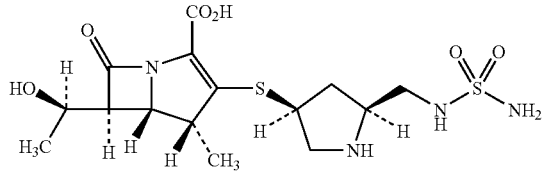

In general, for dissolving a suspension (also referred to as slurry) of a compound, a method of dissolving the suspension by heating it is known.

In a heating step, a continuous heating method, and a batch manner heating method are known. The continuous heating method is a heating method in which only a necessary amount is dissolved by heating to an objective temperature while a majority is placed under the cooling environment, this is successively repeated and, finally, a heated and dissolved one is collected. To the contrary, the batch manner heating method is a heating method in which the suspension continues to undergo heating load until a whole reaches an objective temperature.

For example, in the case of a compound which is unstable to heat, a decomposition amount thereof is influenced by a temperature and a time when exposed to the temperature environment. That is, when a solution in which a compound unstable to heat is dissolved is produced, a whole slurry undergoes heating load, and decomposition of the compound progresses until the compound reaches a goal temperature, and is dissolved, in the case of a batch manner. To the contrary, in the case of a continuous manner, decomposition of a compound is prevented by placing a whole slurry under the cooling environment, the slurry is rapidly elevated in temperature, and dissolved little by little and, after dissolution, the compound is rapidly cooled and crystallized, thereby, decomposition of the compound can be suppressed minimum.

If a whole slurry is dissolved by elevating a temperature in a batch manner, as compared with continuous elevation of a temperature, for example, a required time until the slurry reaches a goal temperature can be around 1/20, depending of a scale.

In addition, as a continuous heating and dissolving equipment which can heat a solution by a continuous heating method, a commercially available machine may be also used.

In addition, Patent Literature 2 describes, as a method of sterilizing a drug composition containing a suspension of a drug, a method comprising a step of rapidly heating the drug composition from an ambient temperature to a high temperature, a step of maintaining a drug composition at the high temperature or at a higher temperature for a certain time, and a step of rapidly cooling the drug composition to an ambient temperature.

[Patent Literature 1]
Japanese Patent No. 2,542,773
[Patent Literature 2]
Japanese Patent Application National Publication (Laid-Open) No. 2004-513749

DISCLOSURE OF THE INVENTION

Problems to be Solved by the Invention

The present inventors found out that doripenem is unstable to heat. Therefore, upon production of an aqueous solution of doripenem, it becomes important to prevent decomposition of doripenem. That is, a method of producing an aqueous solution of doripenem while decomposition of doripenem by heat is prevented has been demanded.

Means to Solve the Problems

The present inventors found out, as a method for producing an aqueous solution of doripenem while decomposition of doripenem by heat is prevented, the following invention.

That is, the present invention relates to:
(1) a process for producing an aqueous solution of doripenem comprising heating to dissolve an aqueous suspension of doripenem with a continuous heating and dissolving equipment by using a dissolving apparatus composed of a container for accommodating a suspension, a continuous heating and dissolving equipment and a container for recovering an aqueous solution,
(2) the process for producing an aqueous solution of doripenem according to the (1), wherein the aqueous suspension is continuously supplied from a container for accommodation in which the aqueous suspension of doripenem is placed, to a continuous heating and dissolving equipment, the aqueous suspension is heated and dissolved in the continuous heating and dissolving equipment, and an aqueous solution of doripenem is continuously recovered from the continuous heating and dissolving equipment,
(3) the process for producing an aqueous solution of doripenem according to the (2), wherein the aqueous suspension of doripenem is passed through the continuous heating and dissolving equipment of an inner diameter of 20 to 26 mm and a length of 25 to 30 m having a heating source at 50 to 70° C., at 4 to 8 L/min,
(4) a process for producing doripenem monohydrate comprising a step of producing an aqueous solution of doripenem by the process as defined in any one of the (1) to (3), and a step of crystallizing doripenem dihydrate from the aqueous solution, and a step of drying the dihydrate crystal,
(5) a process for producing an aqueous solution of doripenem comprising continuously heating an aqueous suspension of doripenem.

Effect of the Invention

According to the present invention, decomposition of doripenem by heat can be prevented, and an aqueous solution of doripenem can be produced effectively.

BEST MODE FOR CARRYING OUT THE INVENTION

The present invention is a process for producing an aqueous solution of doripenem comprising heating to dissolve an aqueous suspension of doripenem with a continuous heating and dissolving equipment.

"Doripenem" is a compound having the following structure described in Japanese Patent No. 2,542,773, which is known as an antibacterial agent. A chemical name is (+)-(4R, 5S,6S)-6-[(1R)-1-hydroxyethyl]-4-methyl-7-oxo-3-[[(3S, 5S)-5-sulfamoylaminomethyl)pyrrolidin-3-yl]thio]1-aza bicyclo[3.2.0]hept-2-ene-2-carboxylic acid).

[Chemical formula 2]

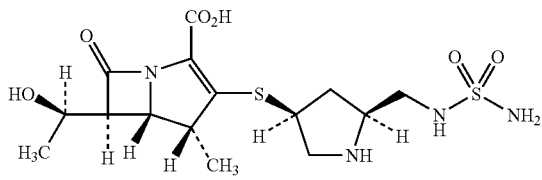

The "aqueous suspension of doripenem" means a liquid in which doripenem is suspended in water, for example, an aqueous suspension in which doripenem is mixed at 50 to 60 g per 1 L of water. It is preferable that an aqueous suspension of doripenem used in the present invention is stored at a room temperature (about 15 to 25° C.) or lower in order to suppress decomposition of doripenem. For example, it is preferable to cool the aqueous suspension to 10° C. or lower. In addition, the present invention is suitable for producing an aqueous solution of a large amount of doripenem from an aqueous suspension of a large amount of doripenem. For example, 200 to 500 L of an aqueous suspension is used. In addition, the aqueous suspension may contain an organic solvent other than water as far as the suspension is in the state where doripenem is suspended. In this case, the finally obtained aqueous solution of doripenem may also contain an organic solvent other than water.

"Heating and dissolving with a continuous heating and dissolving equipment" means that a large amount of an aqueous suspension is not heated at once, but a part of an aqueous suspension is separated from a large amount of an aqueous suspension, the separated aqueous suspension is heated with a continuous heating and dissolving equipment, doripenem is successively dissolved and, from immediately after dissolution, an aqueous solution of doripenem is discharged from the continuous heating and dissolving equipment. By continuously heating, and recovering and cooling an aqueous solution, decomposition of doripenem can be suppressed, and an aqueous solution of doripenem can be produced effectively.

For example, an aqueous solution of doripenem can be produced by accommodating an aqueous suspension of doripenem in an accommodation container, continuously supplying an aqueous suspension of doripenem from the accommodation container stored at the low temperature environment under which decomposition can be suppressed, to a continuous heating and dissolving equipment, heating a supplied aqueous suspension of doripenem in a continuous heating and dissolving equipment to dissolve doripenem, and continuously discharging an aqueous solution of doripenem from the continuous heating and dissolving equipment.

A temperature upon heating and dissolution is preferably 50 to 70° C., particularly preferably 50 to 60° C., further preferably 50 to 55° C. And, a retention time of an aqueous suspension in a continuous heating and dissolving equipment is preferably 130 to 160 seconds. In addition, an optimal retention time varies depending on a heating temperature.

As the continuous heating and dissolving equipment, a commercially available one can be used. By using the continuous heating and dissolving equipment, an aqueous solution of doripenem can be produced while excessive heating generating decomposition unacceptable to doripenem is avoided. That is, by using the continuous heating and dissolving equipment, decomposition of doripenem can be suppressible by heating doripenem at a high temperature but for a short time. An accommodation container for accommodating an aqueous suspension of doripenem is composed, for example, of stainless steel, and can accommodate, for example, a volume of 280 L. Alternatively, a reaction container which can accommodate the same extent of a volume may be used. The accommodation container may be provided with the temperature regulating function in order to suppress decomposition of doripenem in an aqueous suspension. As the continuous heating and dissolving equipment, a continuous heating and dissolving equipment of an inner diameter of 20 to 26 mm (e.g. 25 mm) and a length of 25 to 30 m (e.g. 28 m) is preferable. A continuous heating and dissolving equipment made of stainless steel can be used. A recovery container for recovering an aqueous solution of doripenem is composed of stainless steel, and can accommodate, for example, a volume of 280 L. In addition, in the recovery container, crystallization of doripenem can be performed. The recovery container may be provided with the temperature regulating function in order to suppress decomposition of doripenem in an aqueous solution.

Supplying of an aqueous suspension of doripenem to the continuous heating and dissolving equipment can be performed by press supplying or a pump. For example, when the continuous heating and dissolving equipment of a diameter of 23 mm and a length of 28 m is used, the aqueous suspension may be flown at a flow rate of about 4 to 8 L/min (e.g. 6 L/min).

Alternatively, the accommodation container for an aqueous suspension of doripenem is arranged at an upper part of a continuous heating and dissolving equipment, the recovery container for an aqueous solution of doripenem is arranged at a lower part of the continuous heating and dissolving equipment, and supplying of an aqueous suspension of doripenem to the continuous heating and dissolving equipment may be performed by natural dropping. Thereupon, a dropping rate may be the same extent as that when press supplying or a pump is used.

The present invention includes a process for producing doripenem monohydrate comprising a step of producing an aqueous solution of doripenem by the above process and, further, crystallizing doripenem dihydrate from the resulting aqueous solution of doripenem, and drying the dihydrate crystal (e.g. drying under reduced pressure at 50° C.). Crystallization is performed at a room temperature or under cooling. Before crystallization, working of filtering an aqueous solution of doripenem may be performed using a filter. Production of doripenem monohydrate by crystallization of doripenem dihydrate from an aqueous solution of doripenem, and drying of the dihydrate crystal (e.g. drying under reduced pressure at 50° C.) is disclosed in WO 01/072750.

The present invention includes a process for producing an aqueous solution of doripenem comprising continuously heating an aqueous suspension of doripenem. The present process means a process for producing an aqueous solution of doripenem by excessively heating an aqueous suspension of doripenem not by a batch manner heating method but by a continuous heating method. Specifically, examples include production of an aqueous solution of doripenem by continuously heating an aqueous suspension of doripenem by heating using a continuous heating and dissolving equipment, but the present process is not particularly limited to use of a continuous heating and dissolving equipment as far as it is by a continuous heating method.

EXAMPLE 1

An aqueous suspension of doripenem (aqueous suspension in which 15.5 kg of doripenem had been mixed with 280 L of water) was cooled to 10° C. or lower to suppress decomposition during waiting. This aqueous suspension was passed through a continuous heating and dissolving equipment of an inner diameter of around 23 mm and a length of around 28 m, having a heating source at around 60° C. at about 6 L/min, and elevation in a temperature and dissolution were performed during passage through the machine to obtain an aqueous solution of doripenem at around 55° C. at an outlet of the dissolving machine. A decomposition degree of doripenem at a position of 28 m of the continuous heating and dissolving equipment was about 0.2%. FIG. 1 shows a remaining rate of doripenem at each position of the continuous heating and dissolving equipment.

REFERENCE EXAMPLE 1

Decomposition of doripenem in an aqueous solution of doripenem at 40° C., 50° C., or 60° C. was examined. As a result, it was seen that doripenem is decomposed at these temperatures with time. FIG. 2, FIG. 3 and FIG. 4 show a doripenem decomposition curve at each temperature.

REFERENCE EXAMPLE 2

An aqueous suspension of doripenem (aqueous suspension in which 15.5 kg of doripenem had been mixed with 280 L of water) was cooled to 10° C. or lower to suppress decomposition during waiting. This aqueous suspension was dissolved as it was using a heating medium at around 60° C. to obtain an aqueous solution of doripenem, at around 55° C. A decomposition degree of doripenem measured immediately after dissolution of doripenem was about 7%. FIG. 5 shows a remaining rate of doripenem in the case of a batch manner.

Figure 1:
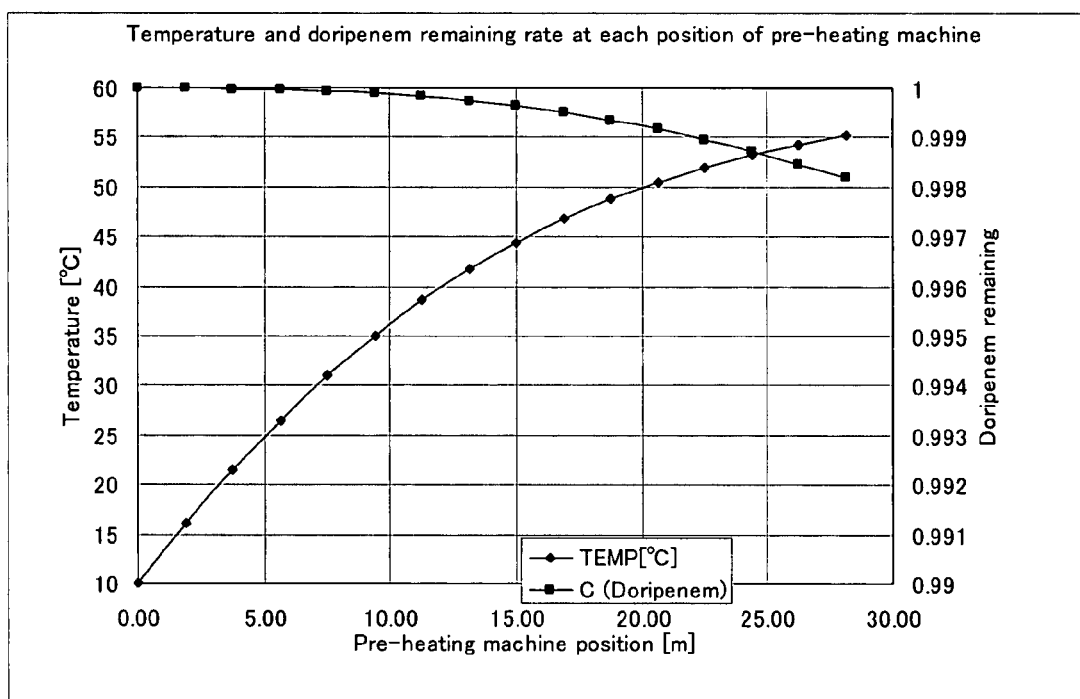
FIG. 1 shows a remaining rate of doripenem at each position of a continuous heating and dissolving equipment.
Figure 2:
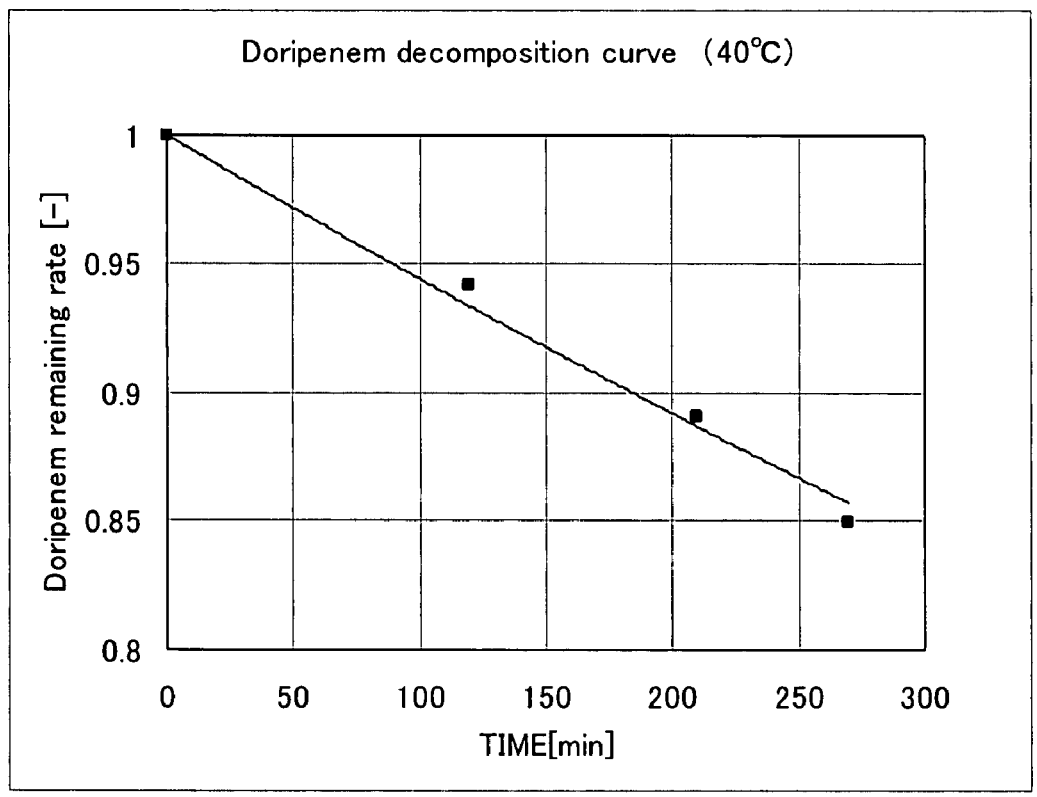
FIG. 2 shows a doripenem decomposition curve at 40 degree.
Figure 3:
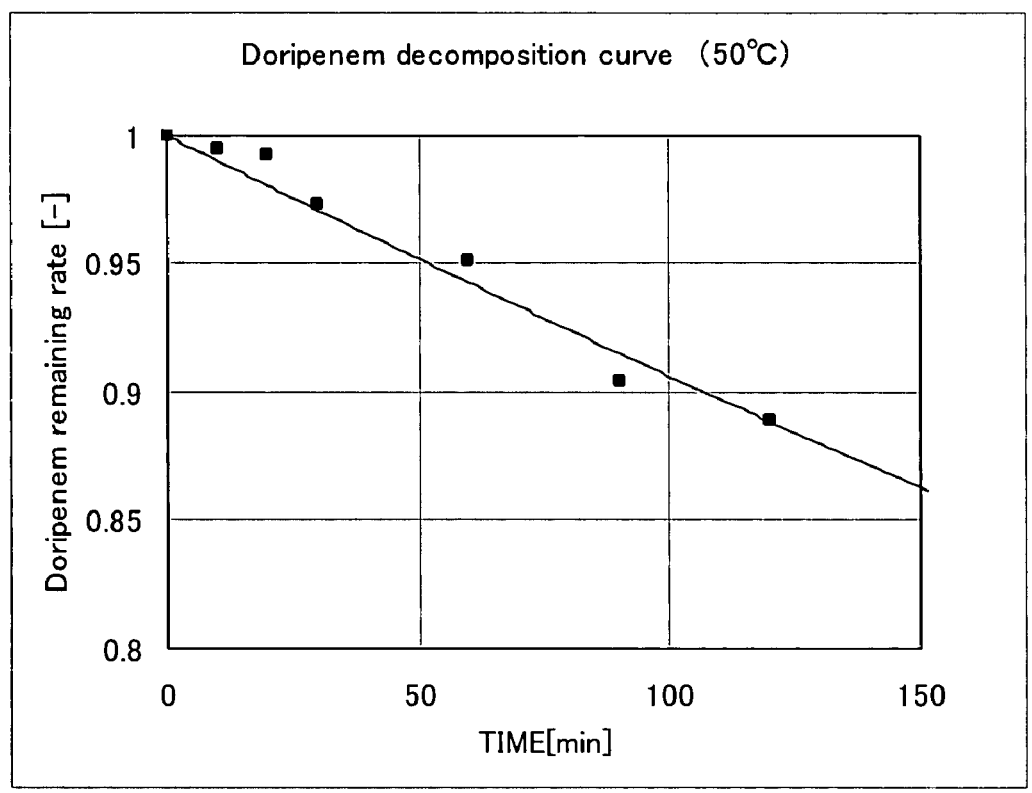
FIG. 3 shows a doripenem decomposition curve at 50 degree.
Figure 4:
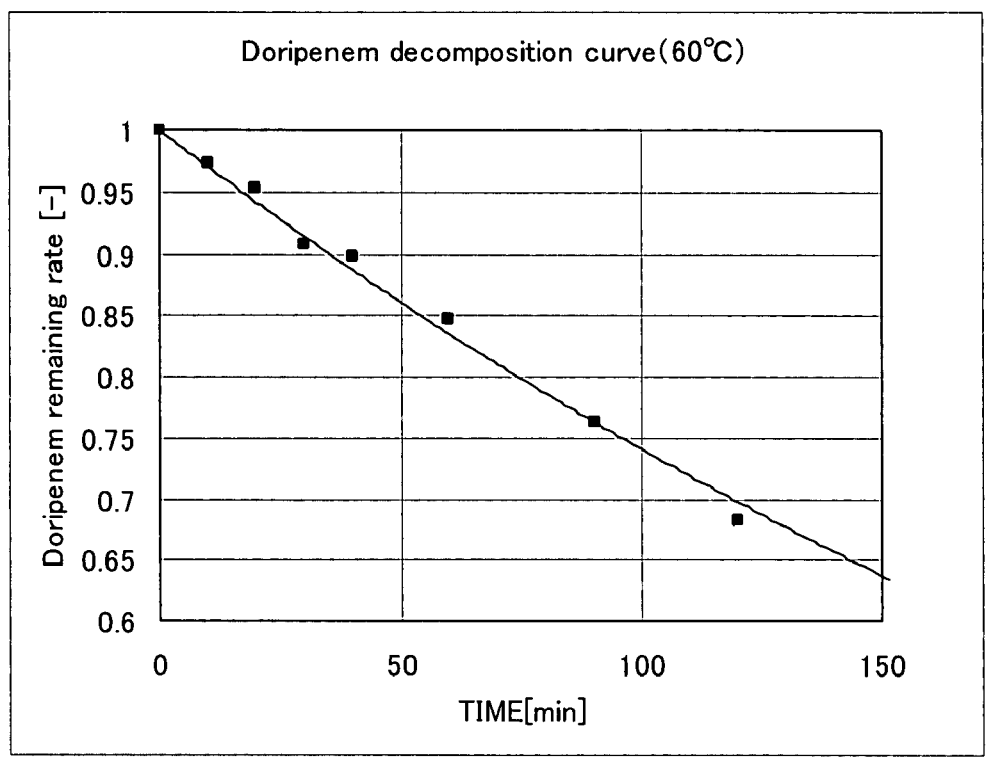
FIG. 4 shows a doripenem decomposition curve at 60 degree.
Figure 5:
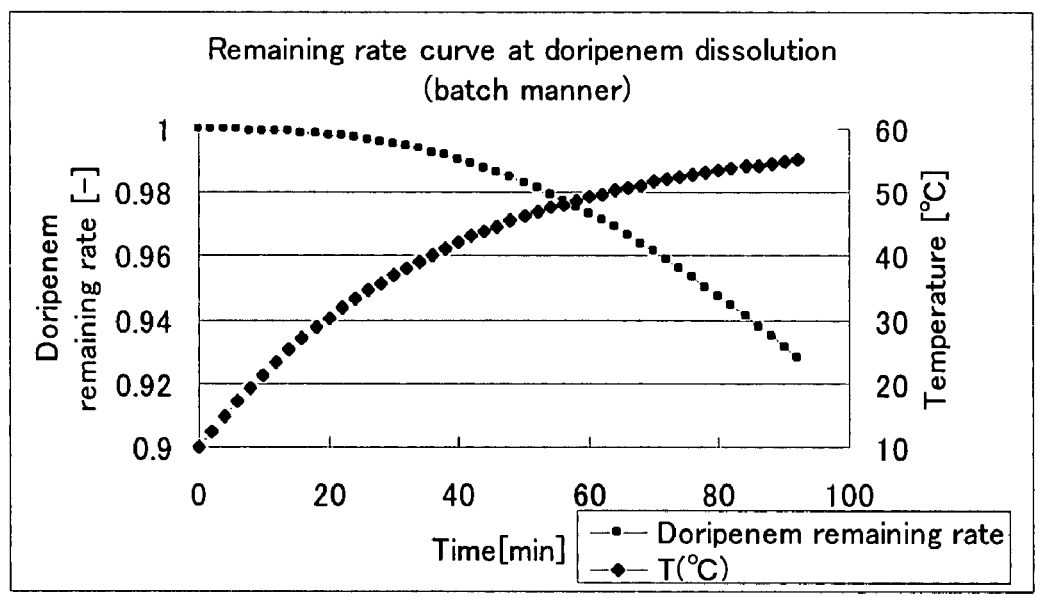
FIG. 5 shows a remaining rate of doripenem in the case of a batch manner.

The invention claimed is:

1. A process for producing an aqueous solution of doripenem comprising heating up to 50 to 70° C. to dissolve an aqueous suspension of doripenem with a continuous heating and dissolving equipment by using a dissolving apparatus composed of a cooled container for accommodating a suspension, a continuous heating and dissolving equipment and a cooled container for recovering an aqueous solution.

2. The process for producing an aqueous solution of doripenem according to claim 1, wherein the aqueous suspension is continuously supplied from the cooled container for accommodation in which the aqueous suspension of doripenem is placed, to the continuous heating and dissolving equipment, the aqueous suspension is heated up to 50 to 70° C. and dissolved in the continuous heating and dissolving equipment, and the aqueous solution of doripenem is continuously recovered from the continuous heating and dissolving equipment to cool.

3. The process for producing an aqueous solution of doripenem according to claim 2, wherein the aqueous suspension of doripenem is passed through the continuous heating and dissolving equipment of an inner diameter of 20 to 26 mm and a length of 25 to 30 m having a heating source at 50 to 70° C., at 4 to 8 L/min.

4. A process for producing doripenem monohydrate comprising a step of producing an aqueous solution of doripenem by the process as defined in claim 1, and a step of crystallizing doripenem dihydrate from the aqueous solution, and a step of drying the dihydrate crystal.

5. A process for producing an aqueous solution of doripenem comprising continuously heating an aqueous suspension of doripenem up to 50 to 70° C.

6. A process for producing doripenem monohydrate comprising a step of producing an aqueous solution of doripenem by the process as defined in claim 2, and a step of crystallizing doripenem dihydrate from the aqueous solution, and a step of drying the dihydrate crystal.

7. A process for producing doripenem monohydrate comprising a step of producing an aqueous solution of doripenem by the process as defined in claim 3, and a step of crystallizing doripenem dihydrate from the aqueous solution, and a step of drying the dihydrate crystal.

* * * * *